United States Patent
Kim et al.

(10) Patent No.: US 10,336,765 B2
(45) Date of Patent: Jul. 2, 2019

(54) DIHYDROPYRANOPYRIMIDINONE DERIVATIVES, AND USE THEREOF

(71) Applicant: St Pharm Co., LTD, Siheung-si (KR)

(72) Inventors: Kyungjin Kim, Siheung-si (KR); Uk-Il Kim, Siheung-si (KR); Ji Hye Yoon, Siheung-si (KR)

(73) Assignee: ST. PHARM CO., LTD. (KR)

( * ) Notice: Subject to any disclaimer, the term of this patent is extended or adjusted under 35 U.S.C. 154(b) by 0 days.

(21) Appl. No.: 16/060,250

(22) PCT Filed: Dec. 1, 2016

(86) PCT No.: PCT/KR2016/014061
§ 371 (c)(1),
(2) Date: Jun. 7, 2018

(87) PCT Pub. No.: WO2017/099424
PCT Pub. Date: Jun. 15, 2017

(65) Prior Publication Data
US 2018/0362538 A1   Dec. 20, 2018

(30) Foreign Application Priority Data
Dec. 8, 2015 (KR) .................. 10-2015-0173801

(51) Int. Cl.
*C07D 491/052* (2006.01)
*A61P 35/00* (2006.01)

(52) U.S. Cl.
CPC .......... *C07D 491/052* (2013.01); *A61P 35/00* (2018.01)

(58) Field of Classification Search
CPC ............................ C07D 491/052; A61P 35/00
USPC ........................................................ 544/278
See application file for complete search history.

(56) References Cited

U.S. PATENT DOCUMENTS

| | | |
|---|---|---|
| 2015/0025070 A1 | 1/2015 | Cheung et al. |
| 2015/0126513 A1 | 5/2015 | Chen et al. |

FOREIGN PATENT DOCUMENTS

| | | |
|---|---|---|
| JP | 2005516053 A | 6/2005 |
| JP | 2014-520858 | 8/2014 |
| JP | 2014-522855 | 9/2014 |
| JP | 2015506965 A | 3/2015 |
| JP | 2015518870 A | 7/2015 |
| WO | 03063874 A1 | 8/2003 |
| WO | WO2013010092 | 1/2013 |
| WO | 2013117288 A1 | 8/2013 |
| WO | 2013182546 A1 | 12/2013 |

OTHER PUBLICATIONS

Lau, T. et al., Cancer Research, 73(10), May 15, 2013.*
Bae, Jeehyeon, et al., Tankyrase 1 Interacts with Mcl-1 Proteins and Inhibits Their Regulation of Apoptosis .J. Biol. Chem., 2003, pp. 5195-5204, vol. 278, No. 7.
Chiang, Y. Jeffrey, et al. "Tankyrase 1 and Tankyrase 2 Are Essential but Redundant for Mouse Embryonic Development" Biochem. J., 2005, pp. 177-184, vol. 391.
Chang, William, et al. "NuMA is a major acceptor of poly(ADP-ribosyl)ation by tankyrase 1 in mitosis", PLoS One, 2008, pp. 177-184, vol. 391.
Chi, Nai-Wen, et al., "Tankyrase Is a Golgi-associated Mitogen-activated Protein Kinase Substrate That Interacts with IRAP in GLUT4 Vesicles", J. Biol. Chem., 2000, pp. 38437-38444, vol. 275.
Huang, Shih-Min et al. "Tankyrase inhibition stabilizes axin and antagonizes Wnt signaling", Nature, 2009, pp. 614-620, vol. 461, No. 7264.
International Search Report dated Feb. 24, 2017, prepared in International Application No. PCT/KR2016/014061.
International Preliminary Report on Patentability dated Jun. 12, 2018, prepared in International Application No. PCT/KR2016/014061.
Lau, Ted, et al., "A Novel Tankyrase Small-Molecule Inhibitor SuppressesAPC Mutation-Driven Colorectal Tumor Growth", Cancer Res., 2013, pp. 3132-3144, vol. 73, No. 10.
Liu, Wanguo, et al., "Mutations in AXIN2 cause colorectal cancer with defective mismatch repair by activating β-catenin/TCF signaling", Nat. Genet., 2000, pp. 146-147, vol. 26.
Miyaki, Michiko, et al. Characteristics of Somatic Mutation of the Adenomatous Polyposis Coli Gene in Colorectal Tumors, Cancer Res., 1994, pp. 3011-3020, vol. 54.
Nkizinkiko, Yves, et al. "Discovery of potent and selective nonplanar tankyrase inhibiting nicotinamide mimics", Bioorganic & Medicinal Chemistry, 2015, 4139-4149, vol. 23.
Taniguchi, Ken, et al., "Mutational spectrum of b-catenin, AXIN1, and AXIN2 in hepatocellular carcinomas and hepatoblastomas", Oncogene, 2002, pp. 4863-4871, vol. 21.
Waaler, Jo, et al. "A Novel Tankyrase Inhibitor Decreases Canonical Wnt Signaling in Colon Carcinoma Cells and Reduces Tumor Growth in Conditional APC Mutant Mice", Cancer Res., 2012, pp. 2822-2832, vol. 72, No. 11.
Wahlberg, Elisabet, et al. "Family wide chemical profiling and structural analysis of PARP and Tankyrase inhibitors", Nat. Biotechnol., 2012, pp. 283-288, vol. 30, No. 3
Shultz, M.D., et al. "Identification of NVP-TNKS656: The use of structure -efficiency relationships to generate a highly potent, selective, and orally active tankyrase inhibitor" J. Med. Chem. 2013, v. 56, pp. 6495-6511.
Ishida, Junya, et al., "4-phenyl-1,2,3,6-tetrahydropyridine, an excellent fragment to improve the potency of PARP-1 inhibitors" Bioorg. Med. Chem. Lett. 2005, v. 15, pp. 4221-4225.

* cited by examiner

*Primary Examiner* — Niloofar Rahmani
(74) *Attorney, Agent, or Firm* — Brinks Gilson & Lione

(57) ABSTRACT

The present invention relates to a novel dihydropyranopyrimidinone derivative, a tautomer thereof, a stereoisomer thereof and their mixture, or a pharmaceutically acceptable salt thereof; and a pharmaceutical composition for preventing or treating a tankyrase-related disease, which contains the same as an active ingredient.

5 Claims, No Drawings

DIHYDROPYRANOPYRIMIDINONE DERIVATIVES, AND USE THEREOF

This application is a National Stage application of International Application No. PCT/KR2016/014061, filed Dec. 1, 2016. This application also claims priority under 35 U.S.C. § 119 to Korean Patent Application No. 10-2015-0173801, filed Dec. 8, 2015.

TECHNICAL FIELD

The present invention relates to a novel dihydropyranopyrimidinone derivative, a tautomer thereof, a stereoisomer thereof and their mixture, or a pharmaceutically acceptable salt thereof; and a pharmaceutical composition for preventing or treating a tankyrase-related disease, which contains the same as an active ingredient; use thereof; and a method treating or preventing a tankyrase-related disease by using the same.

BACKGROUND ART

Human tankyrase belongs to the family of poly(ADP-ribose) polymerase (PARP) proteins which consists of 17 members that share a catalytic PARP domain.

PARP family proteins are promising therapeutic targets. PARP1 and PARP2 play a role in DNA damage responses and PARP inhibitors sensitize cancer cells for drug and radiation therapies. In addition, PARP1 has been linked to other diseases including inflammation, neuronal cell death and ischemia. Tankyrases (TNKS1 and TNKS2), which share high sequence similarity with PARP1, are also emerging therapeutic targets. Tankyrases were initially known as regulators of telomerase activity and are involved in DNA damage responses and Wnt signaling (Wahlbert et al., 2012, *Nat. Biotechnol.*, 30(3): 283-288).

The tankyrase protein family consists of tankyrase 1 (TNKS1) and tankyrase 2 (TNKS2) which share 85% amino acid identity. Biological functions of both tankyrase 1 and tankyrase 2 were studied in genetically engineered mice lacking mouse tankyrase 1 and/or tankyrase 2. Tankyrase 2-deficient mice developed normally and showed no detectable change in telomere length, but did show a significant decrease in total body weight that might reflect a role of tankyrase 2 in glucose or fat metabolism. No defects in telomere length maintenance were detected in tankyrase 1-deficient mice. However, in double-knockout mice lacking both tankyrase 1 and tankyrase 2 embryonic lethality was observed on embryonic day 10 (Chiang et al., 2008, *PLoS One*, 3(7): e2639).

Meanwhile, a key feature of the Wnt/β-catenin pathway is the regulated proteolysis of the downstream effector β-catenin by the β-catenin destruction complex. The principal constituents of a β-catenin destruction complex are adenomatous polyposis *coli* (APC), axin and GSK3α/β. In the absence of Wnt pathway activation, cytosolic β-catenin is constitutively phosphorylated and targeted for degradation. Upon Wnt stimulation, a β-catenin destruction complex is dissociated, which leads to accumulation of β-catenin in the nucleus and transcription of Wnt pathway responsive genes.

It has been recently found that, in the Wnt/β-catenin pathway, a tankyrase inhibitor selectively inhibits the transcription mediated by β-catenin by promoting β-catenin degradation through stabilization of axin (Huang et al., 2009, *Nature*, 461(7264): 614-620).

Inappropriate activation of the pathway, mediated by overexpression of Wnt proteins or mutations affecting the components of the β-catenin destruction complex, thus leading to stabilization of β-catenin, has been observed in many cancers, for example, colon cancer, gastric cancer, hepatocellular carcinoma, breast cancer, medulloblastoma, melanoma, non-small cell lung cancer, pancreatic adenocarcinoma and prostate cancer (Waaler et al., 2012, *Cancer Res.*, 72(11): 2822-2832). Notably, truncating mutations of a tumor suppressor APC are the most prevalent genetic alterations in colorectal carcinomas (Miyaki et al., 1994, *Cancer Res.*, 54: 3011-3020). In addition, Axin1 and Axin2 mutations have been identified in patients with hepatocarcinomas and colorectal carcinomas (Taniguchi et al., 2002, *Oncogene*, 21: 4863-4871; Liu et al., 2000, *Nat. Genet.*, 26: 146-147). These somatic mutations result in Wnt-independent stabilization of β-catenin and constitutive activation of β-catenin-mediated transcription. Furthermore, deregulated Wnt pathway activity has also been implicated in many other non-cancer diseases including osteoporosis, osteoarthritis, polycystic kidney disease, pulmonary fibrosis, diabetes, schizophrenia, vascular diseases, cardiac diseases, non-oncogenic proliferative diseases, neurodegenerative diseases such as Alzheimer's disease, etc.

Therapeutics which are directed to and can correct dysregulation of the Wnt signaling pathway have been implicated in conditions such as bone density defects, coronary disease, late-onset Alzheimer's disease, familial exudative vitreoretinopathy, retinal angiogenesis, tetraamelia, Muellerian-duct regression and virilization, Serkal syndrome, type 2 diabetes, Fuhrmann syndrome, skeletal dysplasia, focal dermal hypoplasia and neural tube defects. Although the introduction has focused on the relevance of Wnt signaling in cancer, the Wnt signaling pathway is of fundamental importance in a broad range of human diseases, not necessarily being limited to the examples provided above for illustrative purposes.

Meanwhile, it has recently been reported that intracellular axin levels are influenced by poly(ADP-ribose) polymerase family members tankyrase-1 and tankyrase-2 (also known as PARP5a and PARP5b) (*Nature Chemical Biology*, 2009, 5: 100; *Nature*, 2009, 461: 614). The tankyrase enzymes are able to poly-ADP ribosylate (PARsylate) axin, which marks this protein for subsequent ubiquitination and proteasomal degradation. Thus, it would be expected that in the presence of an inhibitor of tankyrase catalytic activity, the axin protein concentration would be increased, resulting in higher concentration of the destruction complex, decreased concentration of unphosphorylated intracellular β-catenin and decreased Wnt signaling. An inhibitor of tankyrase-1 and -2 would also be expected to have an effect on other biological functions of tankyrase proteins (e.g., chromosome end (telomere) protection, insulin responsiveness and spindle assembly during mitosis) (Chang et al., 2005, *Biochem. J.*, 391: 177-184; Chi et al., 2000, *J. Biol. Chem.*, 275: 38437-38444; Bae et al., 2003, *J. Biol. Chem.*, 278: 5195-5204).

A novel therapeutic agent that can be used for cancers and hyperproliferative condition.

In particular, it is increasing the need for developing tankyrase inhibitors that modulate the Wnt activity.

DISCLOSURE

Technical Problem

An object of the present invention is a novel compound of inhibiting tankyrase activity, a tautomer thereof, a stereoisomer thereof and their mixture, or a pharmaceutically acceptable salt thereof.

Another object of the present invention is to provide a process for their preparation.

Another object of the present invention is to provide a compound of the present invention, a tautomer thereof, a stereoisomer thereof and their mixture, or a pharmaceutically acceptable salt thereof and a pharmaceutical composition for preventing or treating a tankyrase-related disease, which contains the same as an active ingredient.

Another object of the present invention is to provide a use thereof for the manufacture of a medicament for preventing or treating agent for tankyrase-related disease.

Another object of the present invention is to provide a method of preventing or treating agent for tankyrase-related disease comprising the administration of an effective amount of a therapeutic pharmaceutical composition of the present invention.

Technical Solution

As a result, the present inventors tried to study to achieve the object, and found that the newly designed and synthesized dihydropyranopyrimidinone derivatives can inhibit or regulate tankyrase activity and have completed the present invention:

Dihydropyranopyrimidinone Derivatives

The present invention provides a compound represented by Chemical Formula 1, a tautomer thereof, a stereoisomer thereof and their mixture, or a pharmaceutically acceptable salt thereof:

[Chemical Formula 1]

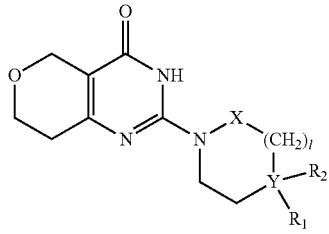

wherein

X is $CHR_4$ or $C=O$;

Y is N or C;

l is 0, 1 or 2;

$R_1$ is hydrogen, hydroxyl, cyano or $C_{1-6}$ alkyl {herein, if Y is N, $R_1$ is null};

$R_2$ is

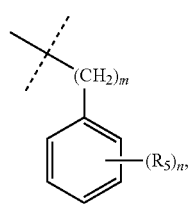

heteroaryl or heterocyclyl;

$R_4$ is hydrogen, hydroxyl, $C_{1-6}$ alkyl or amino;

m is 0, 1, 2 or 3;

n is 0, 1, 2, 3, 4 or 5;

each of $R_5$ is independently —Z—$(CH_2)_p$—$R_6$, halo, cyano, nitro, carboxy, $C_{1-6}$ alkyl, $C_{1-6}$ alkyloxo, $C_{2-6}$ alkenyl, $C_{1-6}$ alkoxy, $C_{1-6}$ alkoxycarbonyl, $C_{1-6}$ hydroxyalkyl, $C_{1-6}$ dihydroxyalkyl, $C_{1-6}$ haloalkyl unsubstituted or optionally substituted with hydroxyl or $C_{3-7}$ cycloalkyl;

Z is —O—, —$S(O)_q$—, —$NR_7$—, —$CONR_7$—, —$CHR_7$— or null;

p is 0, 1, 2, 3, 4, 5 or 6;

q is 0, 1 or 2;

$R_6$ is hydrogen, hydroxyl, —$OR_8$, —O—(C=O)—$R_8$, —$S(O)_r$—$R_8$, cyano, —(C=O)—$R_8$, —(C=O)$OR_8$, —(C=O)$NR_9R_{10}$, —$NR_9R_{10}$, azido, $C_{1-6}$ alkyl, $C_{1-6}$ dihydroxyalkyl, $C_{1-6}$ haloalkyl unsubstituted or optionally substituted with hydroxy, $C_{3-7}$ cycloalkyl, heterocyclyl, $C_{5-10}$ aryl or heteroaryl;

r is 0, 1 or 2;

$R_7$ is hydrogen, $C_{1-6}$ alkyl, $C_{1-6}$ alkoxy, $C_{3-7}$ cycloalkyl or $C_{1-3}$ alkyl-$C_{3-7}$ cycloalkyl;

$R_8$ is hydrogen, $C_{1-6}$ alkyl, $C_{1-6}$ alkyloxo, $C_{1-6}$ alkoxy, amino, $C_{1-6}$ alkylamino, $C_{1-6}$ aminoalkyl, $C_{3-7}$ cycloalkyl, $C_{1-3}$ alkyl—$C_{3-7}$ cycloalkyl or heterocyclyl; each of $R_9$ and $R_{10}$ is independently hydrogen, $C_{1-6}$ alkyl, $C_{1-6}$ alkoxy, $C_{3-6}$ cycloalkyl, $C_{1-3}$ alkyl-$C_{3-6}$ cycloalkyl or —$(SO_2)$—$C_{1-3}$ alkyl;

each of the heteroaryls is a 5- to 10-membered single or fused ring containing one or more heteroatoms selected from the group consisting of N, O, S and a combination thereof, and each of the heterocycles is a 3- to 10-membered single or fused ring containing one or more heteroatoms selected from the group consisting of N, O, S and a combination thereof; one or more hydrogens of each of the cycloalkyls and heterocyclyls may be unsubstituted or substituted with hydroxyl, oxo, halo, cyano, nitro, $C_{1-6}$ alkyl, $C_{1-6}$ hydroxyalkyl, $C_{1-6}$ haloalkyl, $C_{1-6}$ alkoxy, formyl, $C_{1-6}$ alkylformyl, carboxy, $C_{1-6}$ alkylcarboxy, amino, $C_{1-6}$ alkylamino, di($C_{1-6}$ alkyl)amino, carbamoyl, $C_{1-6}$ alkylcarbamoyl or di($C_{1-6}$ alkyl)carbamoyl; and one or more hydrogens of each of the aryls and heteroaryls may be unsubstituted or substituted with hydroxyl, oxo, halo, cyano, nitro, $C_{1-6}$ alkyl, $C_{1-6}$ alkoxy, $C_{1-6}$ hydroxyalkyl, $C_{1-6}$ haloalkyl, pyrazinyl, formyl, $C_{1-6}$ alkylformyl, carboxy, $C_{1-6}$ alkylcarboxy, amino, $C_{1-6}$ alkylamino, di($C_{1-6}$ alkyl)amino, carbamoyl, $C_{1-6}$ alkylcarbamoyl, di($C_{1-6}$ alkyl)carbamoyl or $C_{1-6}$ alkylsulfonyl.

According to an embodiment of the invention, in the above Chemical Formula,

X is $CHR_4$;

Y is N or C;

l is 1 or 2;

$R_1$ is hydrogen, hydroxyl {herein, if Y is N, $R_1$ is null};

$R_2$ is

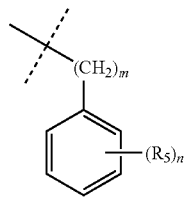

or heteroaryl;

$R_4$ is hydrogen;

m is 0, 1, or 2;

n is 0, 1, 2, or 3;

each of $R_5$ is independently —Z—$(CH_2)_p$—$R_6$, halo or $C_{1-6}$ hydroxyalkyl;

Z is —O— or null;

p is 0, 1, 2, or 3;

$R_6$ is hydrogen, hydroxyl, —$OR_8$, —$NR_9R_{10}$, $C_{1-6}$ dihydroxyalkyl, heterocyclyl or heteroaryl; $R_8$ is hydrogen, $C_{1-6}$ alkyl or heterocyclyl; and each of $R_9$ and $R_{10}$ is independently hydrogen, $C_{1-6}$ alkyl or $C_{3-6}$ cycloalkyl; In the invention, each of the aryls is phenyl or naphthyl, preferably be a phenyl, although it is not limited thereto;

Additionally, each of the heteroaryls is tetrazolyl, imidazolyl, pyridinyl, pyridazinyl, pyrimidyl, triazinyl, pyrrolyl, pyrazolyl, triazolyl, pyrazinyl, furyl, thienyl, isoxazolyl, thiazolyl, isothiazolyl, thiadiazolyl, furazanyl, oxazolyl, indolyl, isoindolyl, indazolyl, quinolinyl, isoquinolinyl, benzothiazolyl, benzoxazolyl, benzofuranyl, benzoimidazolyl, benzotriazolyl or azaindolyl, preferably tetrazolyl or imidazolyl, although it is not limited thereto.

Additionally, each of the heterocyclyls may be tetrahydropyranyl, tetrahydrofuranyl, dihydrofuranyl, dihydropyranyl, dioxanyl, dithianyl, dioxolanyl, imidazolidinyl, imidazolinyl, pyrrolinyl, oxetanyl, pyrrolidinyl, piperidinyl, piperazinyl, morpholinyl, thiomorpholinyl, dioxothiomorpholinyl, dioxotetrahydrothiophenyl, dioxothiolanyl, oxopiperidinyl, oxopyrrolidinyl or oxo-oxazolidinyl, preferably tetrahydrofuranyl, oxetanyl, pyrrolidinyl, piperidinyl, piperazinyl, or morpholinyl, although it is not limited thereto.

According to an embodiment of the invention, the compound may be selected from a group consisting of:

1) 2-(4-(2,6-difluoro-4-(2-methoxyethoxy)phenyl)piperazin-1-yl)-7,8-dihydro-3H-pyrano[4,3-d]pyrimidin-4(5H)-one;

2) 2-(4-(2,6-difluoro-4-(2-morpholinoethoxy)phenyl)piperazin-1-yl)-7,8-dihydro-3H-pyrano[4,3-d]pyrimidin-4(5H)-one;

3) 2-(4-(2,6-difluoro-4-(2-(piperidin-1-yl)ethoxy)phenyl)piperazin-1-yl)-7,8-dihydro-3H-pyrano[4,3-d]pyrimidin-4(5H)-one;

4) 2-(4-(2,6-difluoro-4-(2-hydroxyethoxy)phenyl)piperazin-1-yl)-7,8-dihydro-3H-pyrano[4,3-d]pyrimidin-4(5H)-one;

5) 2-(4-(4-(2,3-dihydroxypropoxy)-2,6-difluorophenyl)piperazin-1-yl)-7,8-dihydro-3H-pyrano[4,3-d]pyrimidin-4(5H)-one;

6) 2-(4-(2,6-difluoro-4-((4-methylpiperazin-1-yl)methyl)phenyl)piperazin-1-yl)-7,8-dihydro-3H-pyrano[4,3-d]pyrimidin-4(5H)-one;

7) 2-(4-(2,6-difluoro-4-(1-hydroxyethyl)phenyl)piperazin-1-yl)-7,8-dihydro-3H-pyrano[4,3-d]pyrimidin-4(5H)-one;

8) 2-(4-(2,6-difluoro-4-(2-methoxyethoxy)phenyl)-4-hydroxypiperidin-1-yl)-7,8-dihydro-3H-pyrano[4,3-d]pyrimidin-4(5H)-one;

9) 2-(4-(2-methyl-2H-tetrazol-5-yl)piperidin-1-yl)-7,8-dihydro-3H-pyrano[4,3-d]pyrimidin-4(5H)-one;

10) 2-(4-(2,6-difluoro-4-(2-oxo-2-(piperidin-1-yl)ethoxy)phenyl)piperazin-1-yl)-7,8-dihydro-3H-pyrano[4,3-d]pyrimidin-4(5H)-one;

11) 2-(4-(2,6-difluoro-4-(2-methoxyethoxy)phenyl)piperidin-1-yl)-7,8-dihydro-3H-pyrano[4,3-d]pyrimidin-4(5H)-one;

12) 2-(4-(4-(2-(diethyl amino)ethoxy)-2,6-difluorophenyl)piperazin-1-yl)-7,8-dihydro-3H-pyrano[4,3-d]pyrimidin-4(5H)-one;

13) 2-(4-(4-(2-(1H-imidazol-1-yl)ethoxy)-2,6-difluorophenyl)piperazin-1-yl)-7,8-dihydro-3H-pyrano[4,3-d]pyrimidin-4(5H)-one.

The compound of Chemical Formula 1 of the present invention may exist in the form of a pharmaceutically acceptable salt. An acid addition salt formed by a pharmaceutically acceptable free acid is useful as the salt. The term "pharmaceutically acceptable salt" used in the present invention refers to any organic or inorganic acid addition salt of the compound represented by Chemical Formula 1 which is at such a concentration that is relatively nontoxic to a patient and has a harmless effective action, and adverse side effects from the salt do not counteract benefits of the compound.

The acid addition salt may be prepared according to a commonly employed method, for example, by dissolving the compound in an excess amount of an aqueous acid solution and precipitating the salt using a water-miscible organic solvent, e.g., methanol, ethanol, acetone or acetonitrile. After heating the compound with an equimolar acid or alcohol (e.g., glycol monomethyl ether) in water, the mixture may be dried via evaporation, or the precipitated salt may be filtered through suction.

Here, a free acid may be an organic acid or an inorganic acid. As an inorganic acid, hydrochloric acid, phosphoric acid, sulfuric acid, nitric acid, stannic acid, etc., may be used and, as an organic acid, methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic and, ascorbic acid, carbonic acid, vanillic acid, or hydroiodic acid, etc. may be used, although it is not limited thereto.

Furthermore, a pharmaceutically acceptable metal salt may be prepared using a base. An alkali metal salt or an alkaline earth metal salt may be obtained, for example, by dissolving the compound in an excess amount of an alkali metal hydroxide or alkaline earth metal hydroxide solution, filtering an undissolved compound salt and then evaporating and drying the filtrate. Preferably, as the metal salt, sodium, potassium or calcium salt may be pharmaceutically suitable, although it is not limited thereto. Also, a corresponding silver salt may be obtained by reacting the alkali metal or alkaline earth metal salt with an appropriate silver salt (e.g., silver nitrate).

Unless specified otherwise, the pharmaceutically acceptable salt of the compound of the present invention includes a plausible acidic or basic salt of the compound of Chemical Formula 1. For example, the pharmaceutically acceptable salt includes sodium, calcium and potassium salts having a hydroxy. In addition, hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts having an amino group may be included as other pharmaceutically acceptable salts. They may be prepared by salt preparation methods known in the art.

The pharmaceutically acceptable salt of dihydropyranopyrimidinone derivative of the present invention may be any pharmaceutically acceptable salt of dihydropyranopyrimidinone derivatives which exhibit inhibitory activity against tankyrase 1 and/or tankyrase 2, which is equivalent to that of dihydropyranopyrimidinone derivative compounds, without limitation.

Synthetic Method of Dihydropyranopyrimidinone Derivatives

The compound of Chemical Formula 1 of the present invention may be synthesized from dihydro-2H-pyran-4(3H)-one via a series of reactions. The following reaction scheme is presented as an exemplary preparation method of the compound of the present invention. However, the method for preparing the compound of the present invention is not limited thereto and a method known in the art may be employed with appropriate modification, if necessary.

Via Reaction Scheme 1 described below, 4-(benzyloxy)-2-(methylsulfonyl)-7,8-dihydro-5H-pyrano[4,3-d]pyrimidine (8) may be synthesized as intermediates.

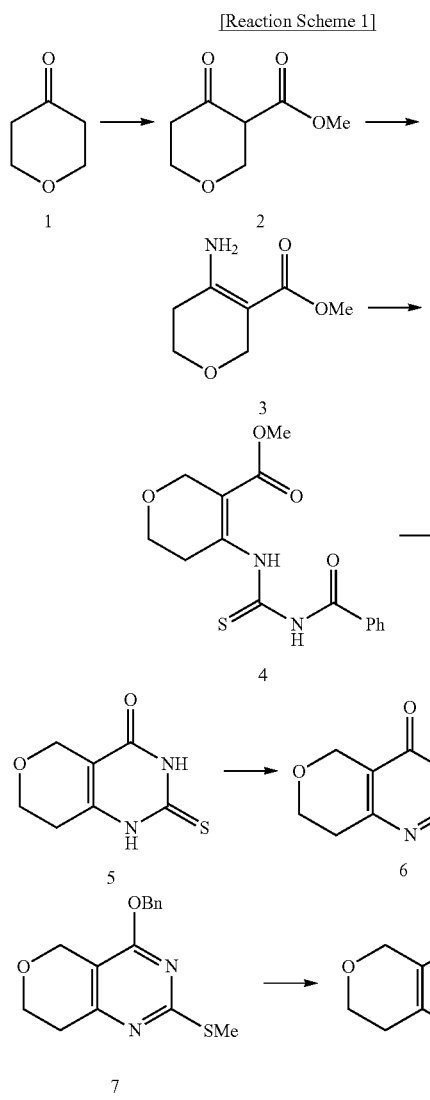

of the present invention can be obtained as fused form of a dihydropyran, benzyl and a pyridine substituted with a methanesulfonyl group.

After the intermediate (8) which constitutes the parent structure of the compound of the present invention is synthesized as described above, a substituent replacing methanesulfonyl group is introduced by further carrying out one or more reaction(s) known in the art.

For example, when the substituent replacing methanesulfonyl group is an amine group, the dihydropyranopyrimidinone derivative compound (10) as the target compound of the present invention may be obtained from the intermediate compound (8) by amination according to the following reaction scheme 2 and, optionally, carrying out amination followed by deprotection if necessary.

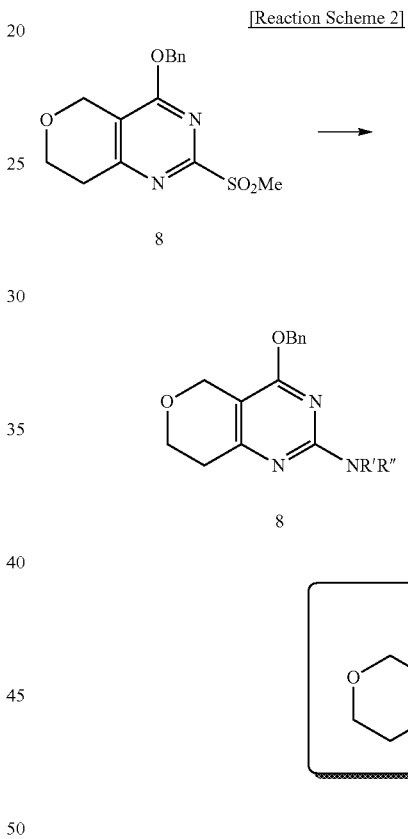

Dihydro-2H-pyran-4(3H)-one (1) reacts with NaH in the presence of dimethylcarbonate in DMF to introduce a methyl ester group (2). Preferably, the reaction may be carried out at 0° C. to rt for 3 h. The product (2) reacts with NH₄OAc in MeOH to form a pyran derivative (3) in which an amino group is introduced. Preferably, the reaction may be carried out at rt for 3 h. Then, reacts with benzoyl isocyanate in THF to form a thiourea group (4), reacts with KOH to induce cyclization. Preferably, the reaction may be carried out at 80° C. to 90° C. for 1 h. The product (5) reacts with KOH and dimethyl sulfate in purified water to introduce a methyl group (6) at S position selectively, reacts with K₂CO₃ and benzyl bromide in DMF to introduce a protecting group (7). Preferably, the reaction may be carried out at rt for 1 h. The product (7) reacted with mCPBA in DCM, thus oxidizing methlythio group. Therefore, dihydropyranopyrimidine (8), a part of a parent structure of the compound Preferably, the amination may be conducted via amination of the intermediate to react with an amine compound containing a substituent suitable for the desired target compound, in THF/EtOH solvent. Preferably, the reaction may be carried out at 120° C. for 3 h to 4 h in microwave reactor.

Compositions Comprising Dihydropyranopyrimidinone Derivative Compounds, Uses Thereof, and Methods of Preventing or Treating Using the Same The present invention provides a pharmaceutical composition for treating or preventing a tankyrase-related disease, which contains the compound of Chemical Formula 1 below, a tautomer thereof, a stereoisomer thereof and their mixture, or a pharmaceutically acceptable salt thereof as an active ingredient.

[Chemical Formula 1]

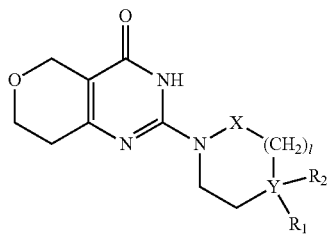

In an aspect, the present invention provides a compound represented by Chemical Formula 1.

The compound of Chemical Formula 1 of the present invention, the tautomer thereof, the stereoisomer thereof and their mixture, or the pharmaceutically acceptable salt thereof may exhibit activity of inhibiting activities of tankyrase 1, tankyrase 2 or both.

Therefore, the pharmaceutical composition containing the compound of Chemical Formula 1 of the present invention as an active ingredient the tautomer thereof, the stereoisomer thereof and their mixture, or the pharmaceutically acceptable salt thereof can prevent or treat tankyrase-related disease by inhibiting the activity of tankyrase 1 and/or tankyrase 2 and thereby regulating cell death proliferation and/or metastasis, it can be usefully used to prevent or treat a disease induced by abnormal activity of tankyrase 1 and/or tankyrase 2.

Specifically, a pharmaceutical composition comprising the compound of the present invention as an active ingredient may be usefully used for the prevention or treatment of a disease selected from the group consisting of a cancer, multiple sclerosis (MS), a cardiovascular disease, central nervous system injury and an inflammatory disease.

The cancer may be selected from the group consisting of a cancer of head, neck, eyes, mouth, throat, esophagus, bronchus, larynx, pharynx, chest, bone, lungs, colon, rectum, stomach, prostate, bladder, uterine, cervix, breast, ovaries, testicles or other reproductive organs, skin, thyroid, blood, lymph nodes, kidneys, liver, pancreas, brain or central nervous system, a solid tumor, a blood-borne tumor, etc. Preferably, the tankyrase-related disease that can be prevented or treated using the pharmaceutical composition of the present invention may be colorectal cancer including colon cancer and rectal cancer, breast cancer, lung cancer or hematological malignancy, although it is not limited thereto.

In the present invention, the term "prevention" refers to any act of inhibiting or retarding the onset, development and recurrence of tankyrase-related diseases by administering the composition of the present invention, and the term "treatment" refers to any act of ameliorating or improving symptoms of the diseases by administering the composition of the present invention.

The pharmaceutical composition according to the present invention may contain 0.1 wt % to 75 wt %, more preferably 1 wt % to 50 wt %, of the compound represented by Chemical Formula 1, the tautomer thereof, the stereoisomer thereof and their mixture, or the pharmaceutically acceptable salt thereof as an active ingredient, based on the total weight of the composition.

The composition of the present invention may further contain a pharmaceutically acceptable carrier, diluent, or excipient, and may be prepared into various formulations including oral formulations such as powder, granule, tablet, capsule, suspension, emulsion, syrup, aerosol, etc., sterile injection solution, etc., according to commonly employed methods. It may be administered orally or via various routes including intravenous, intraperitoneal, subcutaneous, rectal and topical routes. Examples of the suitable carrier, excipient, or diluent that can be contained in the composition may include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. In addition, the composition of the present invention may further contain a filler, an antiaggregant, a lubricant, a wetting agent, a fragrance, an emulsifier, a preservative, etc.

Solid formulations for oral administration may include tablet, pill, powder, granule, capsule, etc. These solid formulations may be prepared by mixing at least one excipient, e.g., starch, calcium carbonate, sucrose, lactose, gelatin, etc., in the composition. In addition to a simple excipient, a lubricant such as magnesium stearate and talc may be used.

Liquid formulations for oral administration may be exemplified by suspension, solution for internal application, emulsion, syrup, etc. In addition to a commonly used simple diluent such as water and liquid paraffin, various excipients such as a wetting agent, a sweetener, an aromatic, a preservative, etc., may be included.

Formulations for parenteral administration may include sterilized aqueous solution, non-aqueous solution, suspension, emulsion, lyophilizate and suppository. For the non-aqueous solution or suspension, propylene glycol, polyethylene glycol, vegetable oil such as olive oil, injectable ester such as ethyl oleate, etc., may be used. As a base for the suppository, Witepsol, macrogol, Tween 61, cacao butter, laurin butter, glycerogelatin, etc., may be used. Meanwhile, injectable formulations may contain commonly used additives such as a solubilizer, an isotonizing agent, a suspending agent, an emulsifier, a stabilizer, a preservative, etc.

The composition of the present invention is administered in a pharmaceutically effective amount. In the present invention, the term "pharmaceutically effective amount" refers to an amount which is sufficient to treat a disease at a reasonable benefit/risk ratio applicable for medical treatment without causing side effects. The level of effective dosage may be determined based on the health condition of a patient, a kind of disease and severity thereof, drug activity, sensitivity to the drug, administration method, administration time, administration route, rate of excretion, treatment period, drugs used in combination or simultaneously and other factors well known in the medical field. The composition of the present invention may be administered as an independent therapeutic agent or in combination with other therapeutic agent(s) sequentially or simultaneously. Also, it may be administered in the form of a single dose or multidoses. It is important to administer an amount that can derive the maximum effects with the minimum amount with no side effects in consideration of all the above-described factors, which can be easily determined by those skilled in the art.

Specifically, the effective amount of the compound in the composition of the present invention may vary depending on the age, sex and body weight of a patient. In general, an amount of 1 mg to 100 mg, preferably 5 mg to 60 mg, per kg body weight may be administered once a day, once in two days or 1 to 3 times a day. However, since the administration dosage can be increased or decreased depending on the administration route, severity of disease, sex, body weight, and age, etc., it does not limit the scope of the present invention by any means.

The present invention also provides a method for preventing or treating a tankyrase-related disease of a subject, which includes administering the compound represented by Chemical Formula 1, the tautomer thereof, the stereoisomer thereof and their mixture, or the pharmaceutically acceptable salt thereof to the subject in need thereof.

In the present invention, the term "subject" refers to an animal in which a tankyrase-related disease has occurred or is likely to occur, including human, monkey, cow, horse, sheep, pig, chicken, turkey, quail, cat, dog, mouse, rat, rabbit or guinea pig. The disease may be effectively prevented or treated by administering the pharmaceutical composition of the present invention to the subject. The pharmaceutical composition of the present invention may be administered in combination with existing therapeutic agent.

In the present invention, the term "administration" refers to introduction of a desired substance to a patient in any appropriate way. The composition of the present invention may be administered via any general administration route as long as it can reach a target tissue. For example, the composition may be administered intraperitoneally, intravenously, intramuscularly, subcutaneously, intradermally, orally, topically, intranasally, intrapulmonarily or rectally, although it is not limited thereto. In addition, the pharmaceutical composition of the present invention may be administered by any apparatus that can deliver an active substance to a target cell. Preferred administration methods and formulations include intravenous injection, subcutaneous injection, intradermal injection, intramuscular injection, bolus injection, etc. The injection may be prepared using water-based solutions such as physiological saline, Ringer's solution, etc., or non-water-based solutions such as vegetable oils, higher fatty acid esters (e.g., ethyl oleate), or alcohols (e.g., ethanol, benzyl alcohol, propylene glycol, glycerin, etc.), and may contain a pharmaceutical excipient such as a stabilizer for preventing denaturation (e.g., ascorbic acid, sodium bisulfife, sodium pyrosulfite, BHA, tocopherol, EDTA, etc.), an emulsifier, a buffer for pH control, a preservative for inhibiting microbial growth (e.g., phenylmercuric nitrate, thimerosal, benzalkonium chloride, phenol, cresol, benzyl alcohol, etc.), etc.

In the present invention, the term "therapeutically effective amount" used in combination with an active ingredient refers to an amount of the dihydropyranopyrimidinone derivative compound, the tautomer thereof, the stereoisomer thereof and their mixture, or the pharmaceutically acceptable salt thereof which is effective in preventing or treating a target disease.

In addition to the dihydropyranopyrimidinone derivative compound, the tautomer thereof, the stereoisomer thereof and their mixture, or the pharmaceutically acceptable salt thereof as the active ingredient, the pharmaceutical composition of the present invention may further comprise a drug used and known for the prevention or treatment of a particular disease depending on a kind of a disease to be prevented or treated. For example, when used for prevention or treatment of a cancer, the composition may further contain, in addition to the dihydropyranopyrimidinone derivative compound, the tautomer thereof, the stereoisomer thereof and their mixture, or the pharmaceutically acceptable salt thereof as the active ingredient, a known anti-cancer agent. Also, other therapies may be used in combination to treat the disease, which include chemotherapy, radiation therapy, hormone therapy, bone marrow transplantation, stem cell replacement therapy, other biological therapies, immunotherapy, etc., although they are not limited thereto.

Examples of anti-cancer agents that can be contained in the pharmaceutical composition of the present invention include a DNA alkylating agent such as mechlorethamine, chlorambucil, phenylalanine, mustard, cyclophosphamide, ifosfamide, carmustine (BCNU), lomustine (CCNU), streptozotocin, busulfan, thiotepa, cisplatin and carboplatin; an anti-cancer antibiotic such as dactinomycin (actinomycin D), doxorubicin (Adriamycin), daunorubicin, idarubicin, mitoxantrone, plicamycin, mitomycin C and bleomycin; and a plant alkaloid such as vincristine, vinblastine, paclitaxel, docetaxel, etoposide, teniposide, topotecan and iridotecan, etc., although they are not limited thereto.

Advantageous Effects

Since a novel dihydropyranopyrimidinone derivative of the present invention can inhibit tankyrase 1 and/or tankyrase 2, it can be effectively used to treat or prevent a disease induced by overexpression or hyperactivation of tankyrases.

BEST MODE

Hereinafter, the constitution and effect of the present invention will be described in more detail through Examples. However, the following Examples are for illustrative purposes only and the scope of the present invention is not limited by the examples.

Preparation Example 1

4-(Benzyloxy)-2-methylsulfonyl)-7,8-dihydro-5H-pyrano[4,3-d]pyrimidine (I-7) as an Intermediate 4-(Benzyloxy)-2-methylsulfonyl)-7,8-dihydro-5H-pyrano[4,3-d]pyrimidine (I-7) was prepared as an intermediate for synthesis of dihydropyranopyrimidinone derivatives based on the following reaction scheme.

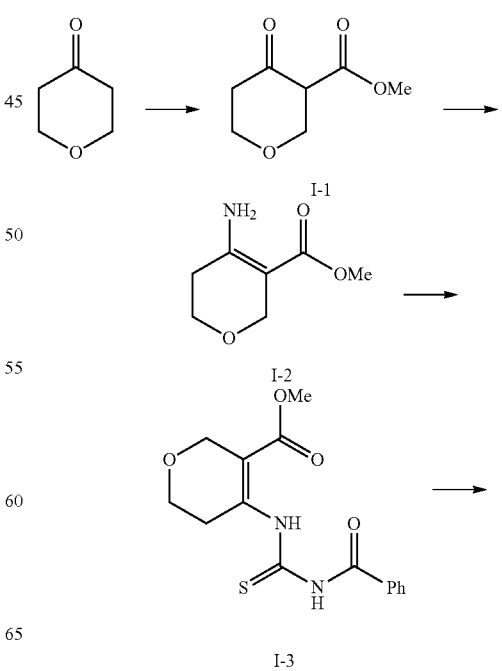

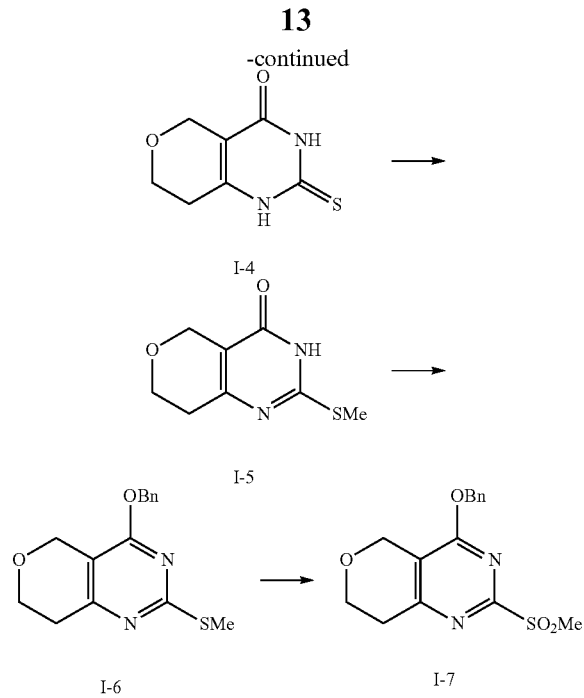

1.1. Methyl 4-oxotetrahydro-2H-pyran-3-carboxylate (I-1)

To a mixture of NaH (1.97 g, 44.96 mmol) in THF (100 ml) was added dropwise dihydro-2H-pyran-4(3H)-one (3 g, 29.96 mmol) in an ice bath. After stirring for 20 min, dimethyl carbonate (3.8 ml, 44.96 mmol) was added. The reaction mixture was stirred at rt for 3 h. To a mixture of diethyl ether/1N HCl was poured reaction mixture with stirring. The organic layer was separated, dried over $Na_2SO_4$, concentrated under reduced pressure and the residue was purified by column chromatography to afford the desired product I-1 (1.5 g) as a yellow liquid.

$^1$H NMR (300 MHz, $CDCl_3$) δ 11.752 (s, 1H), 4.267 (m, 2H), 3.863 (m, 2H), 3.783 (m, 2H), 3.758 (s, 3H), 2.393 (m, 2H), 1.851 (m, 2H).

1.2. Methyl 4-amino-5,6-dihydro-2H-pyran-3-carboxylate (I-2)

To a solution of the compound I-1 (4.75 g, 30.03 mmol) in MeOH (60 ml) was added $NH_4OAc$ (6.95 g, 90.10 mmol). After stirring for 3 h at rt, the reaction mixture was concentrated under reduced pressure and the residue was dissolved in DCM (300 ml). The resulting mixture was washed with water (75 ml), dried over $Na_2SO_4$, filtered, and concentrated under reduced pressure to afford the desired product I-2 (4.72 g) as a white solid.

$^1$H NMR (300 MHz, $CDCl_3$) δ 7.610 (brs, 1H), 6.856 (brs, 1H), 4.126 (s, 3H), 3.647 (t, J=5.7 Hz, 2H), 3.538 (s, 3H), 2.249 (t, J=5.7 Hz, 2H).

1.3. Methyl 4-(3-benzoylthioureido)-5,6-dihydro-2H-pyran-3-carboxylate (I-3)

To a solution of the compound I-2 (4.72 g, 30.03 mmol) in THF (100 ml) was added dropwise benzoyl isothiocyanate (4.84 ml, 36.04 mmol) at 0° C. After stirring for 4 h at rt, the reaction mixture was concentrated under reduced pressure and the residue was diluted with MeOH (15 ml). The resulting mixture was filtered to afford the desired product I-3 (4.33 g) as a yellow solid.

LC-MS (ESI, m/z)=319.1 (M−H$^+$).

1.4. 2-Thioxo-2,3,7,8-tetrahydro-1H-pyrano[4,3-d]pyrimidin-4(5H)-one (I-4)

A mixture of the compound I-3 (8.74 g, 27.28 mmol) and KOH (3.06 g, 54.56 mmol) in 50% EtOH solution (136 ml) was heated to 85° C. while stirring for 1 h. Then, the reaction mixture was allowed to cool down to rt and adjusted to pH 6 to pH 7 by dropwise addition of 6 N HCl. The precipitated was filtered and dried to afford the desired product I-4 (3.8 g) as a white solid.

LC-MS (ESI, m/z)=183.1 (M−H$^+$).

1.5. 2-(methylthio)-7,8-dihydro-3H-pyrano[4,3-d]pyrimidin-4(5H)-one (I-5)

To a mixture of the compound I-4 (3.8 g, 20.63 mmol) and KOH (1.27 g, 22.69 mmol) in water was added dropwise dimethyl sulfate (1.88 ml, 20.63 mmol) over 10 min at 0° C. After stirring for 30 min at rt, the precipitated was filtered to afford the desired product I-5 (3.75 g) as a white solid.

LC-MS (ESI, m/z)=197.1 (M−H$^+$).

1.6. 4-(Benzyloxy)-2-(methylthio)-7,8-dihydro-5H-pyrano[4,3-d]pyrimidine (I-6)

To a solution of the compound I-5 (2.6 g, 13.17 mmol) and $K_2CO_3$ (2.73 g, 19.76 mmol) in DMF (306 ml) was added dropwise benzyl bromide (1.64 ml, 13.83 mmol). After stirring for 1 h at rt, the mixture was diluted with EtOAc, washed with brine for three times, dried over $Na_2SO_4$, concentrated under reduced pressure and the residue was purified by column chromatography to afford the desired product I-6 (1.72 g) as a white solid.

LC-MS (ESI, m/z)=289.0 (M+H$^+$).

1.7. 4-(benzyloxy)-2-(methylsulfonyl)-7,8-dihydro-5H-pyrano[4,3-d]pyrimidine (I-7)

To a solution of the compound I-6 (2.46 g, 8.531 mmol) in DCM (28 ml) was added portionwise mCPBA (4.42 g, 25.59 mmol) at 0° C. The reaction mixture was stirred for 1 h at rt, concentrated under reduced pressure. The residue was diluted with EtOAc, washed with saturated $NaHCO_3$ aqueous solution. The organic layer was dried over $Na_2SO_4$ and concentrated to afford the desired product I-7 (2.24 g) as a white solid.

LC-MS (ESI, m/z)=321.1 (M+H$^+$).

Preparation Example 2

1-(2,6-Difluoro-4-(2-methoxyethoxy)phenyl)piperazine hydrichloride (I-8a) and 1-(2,6-Difluoro-4-(2-(piperidin-1-yl)ethoxy)phenyl)piperazine dihydrochloride (I-8b)

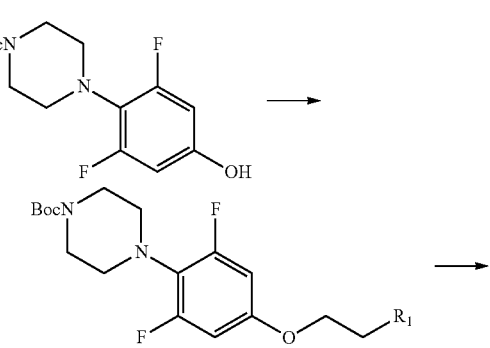

-continued

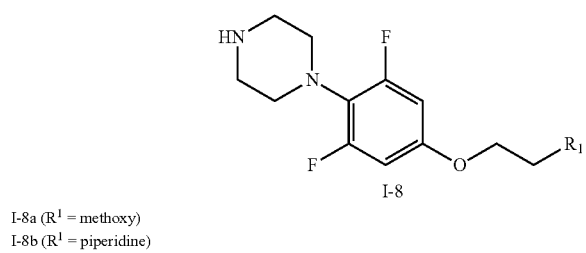

I-8a (R¹ = methoxy)
I-8b (R¹ = piperidine)

2.1. tert-butyl 4-(2,6-difluoro-4-(2-methoxyethoxy)phenyl)piperazine-1-carboxylate tert-butyl 4-(2,6-difluoro-4-hydroxyphenyl)piperazine-1-carboxylate (2 g, 6.363 mmol), 1-bromo-2-methoxyethane (0.72 ml, 7.635 mmol) and $K_2CO_3$ (2.64 g, 19.09 mmol) in DMF was heated to 60° C. to 65° C. After stirring for 16 h, the mixture was allowed to cool down to rt, diluted with EtOAc and washed with water for three times. The organic layer was dried over $Na_2SO_4$ and concentrated under reduced pressure to afford the desired product (2.39 g) as a yellow solid.

LC-MS (ESI, m/z)=373.2 (M+H⁺).

2.2-1. 1-(2,6-Difluoro-4-(2-methoxyethoxy)phenyl)piperazine hydrochloride

To a solution of the compound (2.39 g, 6.363 mmol) obtained in Preparation Example 2.1 in DCM (2 ml) was added 4M HCl (8 ml). After stirring for 2 h at rt, the reaction mixture was concentrated under reduced pressure and the residue was filtered with diethyl ether to afford the desired product I-8a (1.96 g) as a white solid.

LC-MS (ESI, m/z)=273.2 (M+H⁺).

2.2-2. 1-(2,6-Difluoro-4-(2-(piperidin-1-yl)ethoxy)phenyl)piperazine dihydrochloride After alkylation as described in Preparation Example 1.1, the desired product was prepared by removing protection group as same method in Preparation Example 2.2-1.

LC-MS (ESI, m/z)=326.2 (M+H⁺).

Preparation Example 3

3,5-Difluoro-4-(piperazin-1-yl)phenol hydrochloride

By removing protection group of tert-Butyl 4-(2,6-difluoro-4-hydroxyphenyl)piperazine-1-carboxylate, the desired product was prepared by following a similar method to that described in Preparation Example 2.2-1.

LC-MS (ESI, m/z)=215.1 (M+H⁺).

Preparation Example 4

4-(2-(3,5-Difluoro-4-(piperazin-1-yl)phenoxy)ethyl)morpholine dihydrochloride (I-9a), 2-(3,5-difluoro-4-(piperazin-1-yl)phenoxy)-N,N-diethylethanamine dihydrochloride (I-9b) and 1-(4-(2-(1H-imidazol-1-yl)ethoxy)-2,6-difluorophenyl)piperazine hydrochloride (I-9c)

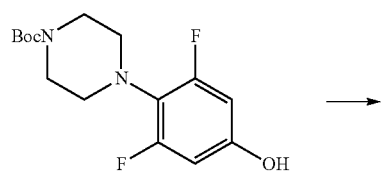

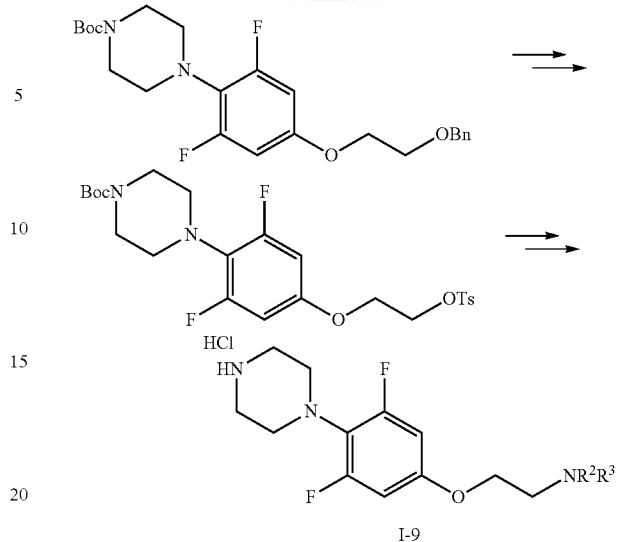

I-9a (R²R³ = morpholine)
I-9b (R²R³ = NEt₂)
I-9c (R²R³ = imidazole)

4.1 tert-butyl 4-(4-(2-(benzyloxy)ethoxy)-2,6-difluorophenyl)piperazine-1-carboxylate Tert-butyl 4-(2,6-difluoro-4-hydroxyphenyl)piperazin-1-carboxylate (1 g, 3.181 mmol), benzyl-2-bromoethylether (851 mg, 3.818 mmol) and $K_2CO_3$ (1.32 g, 9.544 mmol) were dissolved in DMF (6.4 ml). After stirring at 70 to 80° C. for 2 h, the mixture was cooled down to rt. Then, the mixture was diluted by ethylacetate followed by washing 3 times with saturated NaCl aqueous solution. The organic layer was dried over $Na_2SO_4$, concentrated under reduced pressure to afford the desired product (1.427 g) as a yellow liquid.

LC-MS (ESI, m/z)=449.2 (M+H⁺).

4.2 tert-butyl 4-(2,6-difluoro-4-(2-hydroxyethoxy)phenyl)piperazine-1-carboxylate To a solution of the compound (1.427 g, 3.181 mmol) obtained in Preparation Example 4.1 in MeOH (10.6 ml) was added 10% Pd/C (428 mg). After stirring for 2 h under hydrogen gas, the reaction mixture was filtered through a Celite pad. The filtrate was concentrated under reduced pressure to afford the desired product (1.14 g) as an apricot solid.

LC-MS (ESI, m/z)=359.1 (M+H⁺).

4.3 tert-butyl 4-(2,6-difluoro-4-(2-(tosyloxy)ethoxy)phenyl)piperazine-1-carboxylate A mixture of the compound (1.14 g, 3.181 mmol) obtained in Preparation Example 4.2, 4-methylbenzene-1-sulfonyl chloride (909.8 mg, 4.722 mmol), TEA (504 mg, 7.953 mmol) and DMAP (97.2 mg, 0.057 mmol) in DCM (10.6 ml) was stirred at rt. After 3 h, the mixture was diluted with EtOAc, washed with 0.5 N HCl and saturated $NaHCO_3$ aqueous solution. The organic layer was dried over $Na_2SO_4$, concentrated under reduced pressure and filtered with diethyl ether to afford the desired product (1.44 g) as a white solid.

LC-MS (ESI, m/z)=513.2 (M+H⁺).

4.4. tert-butyl 4-(2,6-difluoro-4-(2-morpholinoethoxy)phenyl)piperazine-1-carboxylate A mixture of the compound (700 mg, 1.366 mmol) obtained in Preparation Example 4.3, morpholine (0.14 ml, 1.639 mmol) and $Cs_2CO_3$ (1.11 g, 3.414 mmol) in DMF (4.6 ml) was heated to 65° C. to 70° C. for 17 h. After cooling down to rt, the mixture was diluted with EtOAc and washed with saturated brine for three times. The organic layer was dried over $Na_2SO_4$ and concentrated under reduced pressure to afford the desired product (583 mg) as a yellow liquid.

LC-MS (ESI, m/z)=428.2 (M+H$^+$).

4.5-1 4-(2-(3,5-difluoro-4-(piperazin-1-yl)phenoxy)ethyl)morpholine dihydrochloride (I-9a)

By removing the protection group of the compound (583 mg, 1.366 mmol) obtained Preparation Example 4.4, the desired product (518 mg) as a white solid was prepared by following a similar method to that described in Preparation Example 2.2-1.

LC-MS (ESI, m/z)=328.4 (M+H$^+$).

4.5-2. 2-(3,5-Difluoro-4-(piperazin-1-yl)phenoxy)-N,N-diethylethanamine dihydrochloride (I-9b)

The compound I-9b (377 mg) as a white solid was prepared by the following sequence of reactions: amination used in Preparation Example 4.4 and Boc-group deprotection used in Preparation Example 2.2-1.

LC-MS (ESI, m/z)=314.2 (M+H$^+$).

4.5-3. 1-(4-(2-(1H-imidazol-1-yl)ethoxy)-2,6-difluorophenyl)piperazine hydrochloride (I-9c)

The compound I-9c (530 mg) as a white solid was prepared by the following sequence of reactions: amination used in Preparation Example 4.4 and Boc-group deprotection used in Preparation Example 2.2-1.

LC-MS (ESI, m/z)=309.1 (M+H$^+$).

Preparation Example 5

1-(4-(2-(Benzyloxy)ethoxy)-2,6-difluorophenyl)piperazine hydrochloride

By removing protection group of the compound (1.71 g, 3.818 mmol) obtained in Preparation Example 4.1, the desired product (1.34 g) as a white solid was prepared by following a similar method to that described in Preparation Example 2.2-1.

LC-MS (ESI, m/z)=305.3 (M+H$^+$).

Preparation Example 6

2-(3,5-Difluoro-4-(piperazin-1-yl)phenoxy)-1-(piperidin-1-yl)ethanone hydrochloride 6.1. tert-Butyl 4-(2,6-difluoro-4-(2-oxo-2-(piperidin-1-yl)ethoxy)phenyl)piperazine-1-carboxylate To a solution of piperidine (452.4 mg, 5.313 mmol) in THF (2.5 ml) was added dropwise a solution of 2-chloroacetyl chloride (300 mg, 2.656 mmol) in THF (2.5 ml) over 5 min at 0° C. After stirring for 15 h at rt, the mixture was diluted with EtOAc and washed with water for three times. The organic layer was dried over $Na_2SO_4$ and concentrated under reduced pressure to afford the desired product (507 mg) as a yellow liquid. A mixture of the yellow liquid, 2-chloro-1-(piperidin-1-yl)ethanone (432 mg, 2.67 mmol), tert-butyl 4-(2,6-difluoro-4-hydroxyphenyl)piperazine-1-carboxylate (700 mg, 2.227 mmol) and $K_2CO_3$ (769 mg, 5.567 mmol) in DMF (7.4 ml) was heated to 60° C. to 65° C. for 2 h. The mixture was allowed to cool down to rt, diluted with EtOAc and washed with water for three times. The organic layer was dried over $Na_2SO_4$, concentrated under reduced pressure. The residue was purified by column chromatography to afford the desired product (823 mg) as a white solid.

LC-MS (ESI, m/z)=440.2 (M+H$^+$).

6.2. 2-(3,5-Difluoro-4-(piperazin-1-yl)phenoxy)-1-(piperidin-1-yl)ethanone hydrochloride By removing protection group of the compound (800 mg, 1.820 mmol) obtained in Preparation Example 6.1, the desired product (619 mg) was prepared by following a similar method to that described in Preparation Example 2.2-1.

LC-MS (ESI, m/z)=340.1 (M+H$^+$).

Preparation Example 7

4-(2,6-Difluoro-4-(2-methoxyethoxy)phenyl)piperidin-4-ol hydrochloride 7.1 tert-Butyl 4-(2,6-difluoro-4-(2-methoxyethoxy)phenyl)piperazine-4-hydroxypiperidine-1-carboxylate To a solution of 2-bromo-1,3-difluoro-5-(2-methoxyethoxy)benzene (600 mg, 2.246 mmol) in diethyl ether (20 ml) was added dropwise 2.5M n-BuLi in hexane (0.98 ml, 2.47 mmol) at −78° C. over 10 min. After 30 min, a solution of Boc-piperidone (537 mg, 2.69 mmol) in diethyl ether (4 ml) was added dropwise over 20 min at the same temperature. The reaction mixture was slowly warmed to rt for 1 h while stirring. Upon completion of the reaction, water (15 ml) was added, followed extraction with diethyl ether for three times. The organic layer was dried over $Na_2SO_4$ and concentrated under reduced pressure to afford the desired product (1.01 g) as a yellow liquid.

LC-MS (ESI, m/z)=388.2 (M+H$^+$).

7.2. 4-(2,6-Difluoro-4-(2-methoxyethoxy)phenyl)piperidin-4-ol hydrochloride

Using the compound (1.01 g) obtained in Preparation Example 7.1, the desired product (370 mg) as a white solid was prepared by following a similar method to that described in Preparation Example 2.2-1.

LC-MS (ESI, m/z)=288.1 (M+H$^+$).

Preparation Example 8

4-(2-Methyl-2H-tetrazol-5-yl)piperidine hydrochloride 8.1. tert-Butyl 4-(1H-tetrazol-5-yl)piperidine-1-carboxylate A mixture of tert-butyl 4-cyanopiperidine-1-carboxylate (1 g, 4.75 mmol), sodium azide (923 mg, 14.26 mmol), $NH_4Cl$ (763 mg, 14.26 mmol) in DMF (9.4 ml) was stirred at 140° C. for 20 h. Upon completion of the reaction, the mixture was cooled down and diluted with EtOAc (200 ml), followed by washing with 0.5 N HCl and water. The organic layer was dried over $Na_2SO_4$, concentrated under reduced pressure, the residue was diluted with diethyl ether and filtered to afford the desired product (764 mg) as a white solid.

LC-MS (ESI, m/z)=254.1 (M+H$^+$).

8.2. 4-(2-Methyl-2H-tetrazol-5-yl)piperidine hydrochloride

The compound (1 g, 3.95 mmol) obtained in Preparation Example 8.1 was reacted with MeI by following a similar method to that described in Preparation Example 4.4. The mixture was diluted with EtOAc and washed with water for three times. The organic layer was dried over $Na_2SO_4$, concentrated under reduced pressure. By removing deprotection group as a similar method to that described in Preparation Example 2.2-1, the residue was purified by column chromatography to afford the desired product (518 mg) as a white solid.

LC-MS (ESI, m/z)=168.1 (M+H$^+$).

Preparation Example 9

1-(3,5-Difluoro-4-(piperazin-1-yl)benzyl)-4-methyl-piperazine dihydrochloride 9.1. tert-Butyl 4-(2,6-difluoro-4-formylphenyl)piperazine-1-carboxylate A mixture of 3,4,5-trifluorobenzaldehyde (2 g, 12.493 mmol), Boc-piperazine (2.33 g, 12.493 mmol) and $K_2CO_3$ (3.45 g, 24.986 mmol) in DMF (4 ml) was stirred at 110° C. to 120° C. for 18 h. After cooling down to rt, the mixture was diluted with EtOAc (250 ml) and washed with water for three times. The organic layer was dried over $Na_2SO_4$, concentrated under reduced pressure and the residue was purified by column chromatography to afford the desired product (2.7 g) as a yellow solid.

LC-MS (ESI, m/z)=327.1 (M+H$^+$).

9.2. tert-Butyl 4-(2,6-difluoro-4-((4-methylpiperazin-1-yl)methyl)phenyl)piperazine-1-carboxylate A mixture of the compound (700 mg, 2.145 mmol) obtained in Preparation Example 9.1, methylpiperazine (0.48 ml, 4.29 mmol) and Ti(i-Pro)$_4$ (1.27 ml, 4.29 mmol) in MeOH (6 ml) was stirred for 17 h at rt, followed by cooling down to 0° C. Then, NaCNBH$_3$ (270 mg, 4.29 mmol) was added to the reaction mixture at 0° C. After stirring for 5 h at rt, the mixture was concentrated under reduced pressure, and the residue was filtered through a Celite pad using DCM. The resulting mixture was diluted with DCM (200 ml), washed with water for three times, dried over $Na_2SO_4$ and concentrated under reduced pressure. The residue was purified by column chromatography to afford the desired product (435 mg) as a colorless liquid.

LC-MS (ESI, m/z)=411.3 (M+H$^+$).

9.3. 1-(3,5-Difluoro-4-(piperazin-1-yl)benzyl)-4-methyl-piperazine dihydrochloride By reacting the compound (435 mg, 1.060 mmol) obtained in Preparation Example 9.2, the desired product (428 mg) as a white solid was prepared by following a similar method to that described in Preparation Example 2.2-1.

LC-MS (ESI, m/z)=311.1 (M+H$^+$).

Preparation Example 10

1-(4-(1-(Benzyloxy)ethyl)-2,6-difluorophenyl)piperazine hydrochloride 10.1. tert-Butyl 4-(2,6-difluoro-4-(1-hydroxyethyl)phenyl)piperazine-1-carboxylate To a solution of the compound (600 mg, 1,839 mmol) obtained in Preparation Example 9.1 in THF (5 ml) was added dropwise a solution of 1.6 M MeLi in diethyl ether (1.26 ml, 2.023 mmol) at −78° C. The reaction mixture was slowly warmed to rt. While stirring for 2 h, the mixture was concentrated under reduced pressure, the residue was diluted with EtOAc (40 ml), washed with water. The organic layer was dried over $Na_2SO_4$, concentrated under reduced pressure and the residue was purified by column chromatography to afford the desired product (503 mg) as a yellow solid.

LC-MS (ESI, m/z)=342.2 (M+H$^+$).

10.2. tert-Butyl 4-(4-(1-(benzyloxy)ethyl)-2,6-difluorophenyl)piperazine-1-carboxylate To a solution of the compound (300 mg, 0.876 mmol) obtained in Preparation Example 10.1 in THF (3 ml) was added NaH (63 mg, 1.314 mmol) at 0° C. After stirring for 10 min, a solution of benzyl bromide (0.13 ml, 1.051 mmol) in THF (0.5 ml) was added dropwise to the reaction mixture. The mixture was stirred for 6 h at rt, diluted with EtOAc and washed with water. The organic layer was dried over $Na_2SO_4$, concentrated under reduced pressure and the residue was purified by column chromatography to afford the desired product (314 mg) as a colorless liquid.

LC-MS (ESI, m/z)=433.2 (M+H$^+$).

10.3. 1-(4-(1-(Benzyloxy)ethyl)-2,6-difluorophenyl)piperazine hydrochloride

By reacting the compound (314 mg, 0.726 mmol) obtained in Preparation Example 10.2, the desired product (227 mg) as an apricot solid was prepared by following a similar method to that described in Preparation Example 2.2-1.

LC-MS (ESI, m/z)=333.2 (M+H$^+$).

Example 1

2-(4-(2,6-Difluoro-4-(2-methoxyethoxy)phenyl)piperazin-1-yl)-7,8-dihydro-3H-pyrano[4,3-d]pyrimidin-4(5H)-one Step 1: To a microwave reaction vial were added the compound I-7 (200 mg, 0.624 mmol), the compound I-8a (231 mg, 0.749 mmol), EtOH (1 ml), THF (1 ml) and DIPEA (0.27 ml, 1.561 mmol). The reaction mixture was heated at 120° C. under microwave heating condition for 3 h. The mixture was diluted with EtOAc, washed with water, dried over $Na_2SO_4$, concentrated under reduced pressure and the residue was purified by column chromatography to afford the desired product (70 mg) as a yellow liquid.

LC-MS (ESI, m/z)=513.2 (M+H$^+$).

Step 2: To a solution of the compound (80 mg, 0.351 mmol) obtained in Step 1 in MeOH (0.6 ml) and DCM (0.6 ml) was added 10% Pd/C (90 mg). The reaction mixture was stirred for 1 h under hydrogen gas. Upon completion of the reaction, the mixture was filtered through a Celite pad. The filtrate was concentrated under reduced pressure, the residue was diluted with IPA and filtered to afford the desired product (88 mg) as a white solid.

LC-MS (ESI, m/z)=423.1 (M+H$^+$).

Example 2

2-(4-(2,6-Difluoro-4-(2-molpholinoethoxy)phenyl)piperazin-1-yl)-7,8-dihydro-3H-pyrano[4,3-d]pyrimidin-4(5H)-one The compound (I-9a) obtained in Preparation Example 4.5, was reacted with the compound I-7 in the same manner as described in Example 1 to afford the desired product.

LC-MS (ESI, m/z)=478.2 (M+H$^+$).

Example 3

2-(4-(2,6-Difluoro-4-(2-(piperidin-1-yl)ethoxy)phenyl)piperazin-1-yl)-7,8-dihydro-3H-pyrano[4,3-d]pyrimidin-4(5H)-one The compound (I-8b) obtained in Preparation Example 2.2-2, was reacted with the compound I-7 in the same manner as described in Example 1 to afford the desired product.

LC-MS (ESI, m/z)=476.2 (M+H$^+$).

Example 4

2-(4-(2,6-Difluoro-4-(2-hydroxyethoxy)phenyl)piperazin-1-yl)-7,8-dihydro-3H-pyrano[4,3-d]pirimidin-4(5H)-one The compound obtained in Preparation Example 5, was reacted with the compound I-7 in the same manner as described in Example 1 to afford the desired product.
LC-MS (ESI, m/z)=409.1 (M+H$^+$).

Example 5

2-(4-(4-(2,3-Dihydroxypropoxy)-2,6-difluorophenyl)piperazin-1-yl)-7,8-dihydro-3H-pyrano[4,3-d]pyrimidin-4(5H)-one The desired product was prepared by the following sequence of reactions: reaction of the compound I-7 obtained in Preparation Example 1.7 with the compound obtained in Preparation Example 3 by the method as described in Example 1 Step 1, alkylation with (2,2-dimethyl-1,3-dioxolan-4-yl)methyl 4-methylbenzenesulfonate, acetonide deprotection using TFA and debenzylation used in Example 1 Step 2.
LC-MS (ESI, m/z)=439.1 (M+H$^+$).

Example 6

2-(4-(2,6-Difluoro-4-((4-methylpiperazin-1-yl)methyl)phenyl)piperazin-1-yl)-7,8-dihydro-3H-pyrano[4,3-d]pyrimidin-4(5H)-one The compound obtained in Preparation Example 9.3, was reacted with the compound I-7 in the same manner as described in Example 1 to afford the desired product.
LC-MS (ESI, m/z)=461.2 (M+H$^+$).

Example 7

2-(4-(2,6-Difluoro-4-(1-hydroxyethyl)phenyl)piperazin-1-yl)-7,8-dihydro-3H-pyrano[4,3-d]pyrimidin-4(5H)-one The compound obtained in Preparation Example 10.3, was reacted with the compound 1-7 in the same manner as described in Example 1 to afford the desired product.
LC-MS (ESI, m/z)=393.1 (M+H$^+$).

Example 8

2-(4-(2,6-Difluoro-4-(2-methoxyethoxy)phenyl)-4-hydroxypiperidine-1-yl)-7,8-dihydro-3H-pyrano[4,3-d]pyrimidin-4(5H)-one The compound obtained in Preparation Example 7.2, was reacted with the compound 1-7 in the same manner as described in Example 1 Step 1 to afford the desired product and 4-(benzyloxy)-2-(4-(2,6-difluoro-4-(2-metoxyethoxy)phenyl)-5,6-dihydropyridin-1(2H)-yl)-7,8-dihydro-5H-pyrano[4,3-d]pyrimidine was obtained as a side product. The desired product was prepared by following a similar method to that described in Example 1 Step 2.
LC-MS (ESI, m/z)=438.2 (M+H$^+$).

Example 9

2-(4-(2-Methyl-2H-tetrazol-5-yl)piperidin-1-yl)-7,8-dihydro-3H-pyrano[4,3-d]pyrimidin-4(5H)-one The compound obtained in Preparation Example 8.2, was reacted with the compound 1-7 in the same manner as described in Example 1 to afford the desired product.
LC-MS (ESI, m/z)=318.1 (M+H$^+$).

Example 10

2-(4-(2,6-Difluoro-4-(2-oxo-2-(piperidin-1-yl)ethoxy)phenyl)piprazin-1-yl)-7,8-dihydro-3H-pyrano[4,3-d]pyrimidin-4(5H)-one The compound obtained in Preparation Example 6.2, was reacted with the compound I-7 in the same manner as described in Example 1 to afford the desired product.
LC-MS (ESI, m/z)=490.2 (M+H$^+$).

Example 11

2-(4-(2,6-Difluoro-4-(2-methoxyethoxy)phenyl)piperidin-1-yl)-7,8-dihydro-3H-pyrano[4,3-d]pyrimidin-4(5H)-one 4-(Benzyloxy)-2-(4-(2,6-difluoro-4-(2-methoxyethoxy)phenyl)-5,6-dihydropyridin-1(2H)-yl)-7,8-dihydro-5H-pyrano[4,3-d]pyrimidine obtained in Example 8 as a side product, was reacted with the compound I-7 in the same manner as described in Example 1 Step 2 to afford the desired product.
LC-MS (ESI, m/z)=422.1 (M+H$^+$).

Example 12

2-(4-(4-(2-(Diethylamino)ethoxy)-2,6-difluorophenyl)piperazin-1-yl)-7,8-dihydro-3H-pyrano[4,3-d]pyrimidin-4(5H)-one The compound obtained in Preparation Example 4.5-2, was reacted with the compound 1-7 in the same manner as described in Example 1 to afford the desired product.
LC-MS (ESI, m/z)=464.3 (M+H$^+$).

Example 13

2-(4-(4-(2-(1H-imidazol-1-yl)ethoxy)-2,6-difluorophenyl)piperazin-1-yl)-7,8-dihydro-3H-pyrano[4,3-d]pyrimidin-4(5H)-one The compound obtained in Preparation Example 4.5-3, was reacted with the compound 1-7 in the same manner as described in Example 1 to afford the desired product.
LC-MS (ESI, m/z)=459.1 (M+H$^+$).

Example 14

Analysis of Activity of Tankyrase 1

Activities of novel compounds synthesized according to Examples 1 to 13 against tankyrase 1 were analyzed using a Trevigen kit (Cat. No. 4700-096-K). Poly PAR histone protein-coated 96-well plate, anti-PAR monoclonal antibody and goat anti-mouse IgG-HRP were used for measurement of absorbance by ELISA method. Specifically, 20×I-PAR assay buffer was diluted to 1× by adding water, and 50 µL of the diluted buffer was added to each well of the 96-well plate followed by reacting at rt for 30 min. Then, the supernatant was completely removed from each well and 10 µL of 1×I-PAR assay buffer and 15 µL of assay substrate were added to each well along with 1 µL of a 50× solution of inhibitors to be tested, which were the compounds obtained in the Examples 1 to 13. 10 mUnits/µL of tankyrase 1 enzyme was diluted 50-fold with 1×I-PAR assay buffer and 25 µL of the diluted enzyme was added to each well and reacted while stirring at rt for 30 min. One without any compound of the present invention was used as a positive control and another containing 1×I-PAR assay buffer with the same volume instead of tankyrase 1 enzyme was used as a negative control.

Upon completion of the reaction, 200 µL of PBSX, which was prepared by adding 0.1% triton X-100 to PBS, was added and removed and this washing process was repeated twice. Washing was repeated twice more using PBS in the same manner. 5× antibody diluent was diluted with distilled water to 1× concentration, 50 µL of the diluted goat anti-mouse IgG-HRP to 1/2000 was added to each well and reacted while stirring at rt for 30 min. Washes were carried out twice using PBSX and PBS, respectively. After adding 50 µL of TACS-sapphire to each well of the plate, the plate was blocked from light to react for 10 min to 15 min and the color of the reaction solution turned blue. To stop the reaction, 50 µL of 0.2N HCl was added to turn the solution yellow. Finally, the absorbance of the resulting solution was measured at 450 nm.

TABLE 1

| No. | R | IUPAC Name | TNKS1 (IC$_{50}$, nM) |
|---|---|---|---|
| 1 | 4-(2,6-difluoro-4-(2-methoxyethoxy)phenyl)piperazin-1-yl | 2-(4-(2,6-difluoro-4-(2-methoxyethoxy)phenyl)piperazin-1-yl)-7,8-dihydro-3H-pyrano[4,3-d]pyrimidin-4(5H)-one | 27.2 |
| 2 | 4-(2,6-difluoro-4-(2-morpholinoethoxy)phenyl)piperazin-1-yl | 2-(4-(2,6-difluoro-4-(2-morpholinoethoxy)phenyl)piperazin-1-yl)-7,8-dihydro-3H-pyrano[4,3-d]pyrimidin-4(5H)-one | 40.6 |
| 3 | 4-(2,6-difluoro-4-(2-(piperidin-1-yl)ethoxy)phenyl)piperazin-1-yl | 2-(4-(2,6-difluoro-4-(2-(piperidin-1-yl)ethoxy)phenyl)piperazin-1-yl)-7,8-dihydro-3H-pyrano[4,3-d]pyrimidin-4(5H)-one | 40.3 |
| 4 | 4-(2,6-difluoro-4-(2-hydroxyethoxy)phenyl)piperazin-1-yl | 2-(4-(2,6-difluoro-4-(2-hydroxyethoxy)phenyl)piperazin-1-yl)-7,8-dihydro-3H-pyrano[4,3-d]pyrimidin-4(5H)-one | 26.6 |

TABLE 1-continued

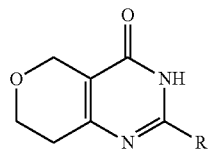

| No. | R | IUPAC Name | TNKS1 (IC$_{50}$, nM) |
|---|---|---|---|
| 5 | | 2-(4-(4-(2,3-dihydroxypropoxy)-2,6-difluorophenyl)piperazin-1-yl)-7,8-dihydro-3H-pyrano[4,3-d]pyrimidin-4(5H)-one | 26.1 |
| 6 | | 2-(4-(2,6-difluoro-4-((4-methylpiperazin-1-yl)methyl)phenyl)piperazin-1-yl)-7,8-dihydro-3H-pyrano[4,3-d]pyrimidin-4(5H)-one | 36.8 |
| 7 | | 2-(4-(2,6-difluoro-4-(1-hydroxyethyl)phenyl)piperazin-1-yl)-7,8-dihydro-3H-pyrano[4,3-d]pyrimidin-4(5H)-one | 21.8 |
| 8 | | 2-(4-(2,6-difluoro-4-(2-methoxyethoxy)phenyl)-4-hydroxypiperidin-1-yl)-7,8-dihydro-3H-pyrano[4,3-d]pyrimidin-4(5H)-one | 162.5 |
| 9 | | 2-(4-(2-methyl-2H-tetrazol-5-yl)piperidin-1-yl)-7,8-dihydro-3H-pyrano[4,3-d]pyrimidin-4(5H)-one | 803.3 |
| 10 | | 2-(4-(2,6-difluoro-4-(2-oxo-2-(piperidin-1-yl)ethoxy)phenyl)piperazin-1-yl)-7,8-dihydro-3H-pyrano[4,3-d]pyrimidin-4(5H)-one | 34.2 |

TABLE 1-continued

| No. | R | IUPAC Name | TNKS1 (IC$_{50}$, nM) |
|---|---|---|---|
| 11 | (piperidine with 2,6-difluoro-4-(2-methoxyethoxy)phenyl) | 2-(4-(2,6-difluoro-4-(2-methoxyethoxy)phenyl)piperidin-1-yl)-7,8-dihydro-3H-pyrano[4,3-d]pyrimidin-4(5H)-one | 74.4 |
| 12 | (piperazine with 4-(2-(diethylamino)ethoxy)-2,6-difluorophenyl) | 2-(4-(4-(2-(diethylamino)ethoxy)-2,6-difluorophenyl)piperazin-1-yl)-7,8-dihydro-3H-pyrano[4,3-d]pyrimidin-4(5H)-one | 33.6 |
| 13 | (piperazine with 4-(2-(1H-imidazol-1-yl)ethoxy)-2,6-difluorophenyl) | 2-(4-(4-(2-(1H-imidazol-1-yl)ethoxy)-2,6-difluorophenyl)piperazin-1-yl)-7,8-dihydro-3H-pyrano[4,3-d]pyrimidin-4(5H)-one | 25.4 |

The invention claimed is:

1. A compound represented by Chemical Formula 1, a tautomer thereof, a stereoisomer thereof and their mixture, or a pharmaceutically acceptable salt thereof:

[Chemical Formula 1]

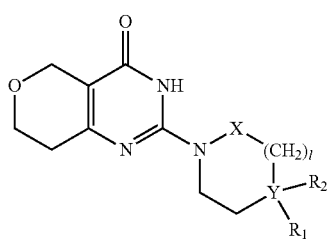

wherein,

X is CHR$_4$ or C=O;

Y is N or C;

l is 0, 1, or 2;

R$_1$ is hydrogen, hydroxyl, cyano or C$_{1-6}$ alkyl {herein, if Y is N, R$_1$ is null};

R$_2$ is

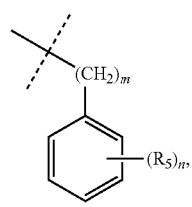

heteroaryl or heterocyclyl;

R$_4$ is hydrogen, hydroxyl, C$_{1-6}$ alkyl or amino;

m is 0, 1, 2 or 3;

n is 0, 1, 2, 3, 4 or 5;

each of R$_5$ is independently —Z—(CH$_2$)$_p$—R$_6$, halo, cyano, nitro, carboxy, C$_{1-6}$ alkyl, C$_{1-6}$ alkyloxo, C$_{2-6}$ alkenyl, C$_{1-6}$ alkoxy, C$_{1-6}$ alkoxycarbonyl, C$_{1-6}$ hydroxyalkyl, C$_{1-6}$ dihydroxyalkyl, C$_{1-6}$ haloalkyl unsubstituted or optionally substituted with hydroxyl or C$_{3-7}$ cycloalkyl;

Z is —O—, —S(O)$_q$—, —NR$_7$—, —CONR$_7$—, —CHR$_7$—, or null;

p is 0, 1, 2, 3, 4, 5 or 6;

q is 0, 1 or 2;

R$_6$ is hydrogen, hydroxyl, —OR$_8$, —O—(C=O)—R8, —S(O)$_r$—R$_8$, cyano, —(C=O)—R$_8$, —(C=O)OR$_8$, —(C=O)NR$_9$R$_{10}$, —NR$_9$R$_{10}$, azido, C$_{1-6}$ alkyl, C$_{1-6}$ dihydroxyalkyl, C$_{1-6}$ haloalkyl unsubstituted or optionally substituted with hydroxyl, C$_{3-7}$ cycloalkyl, heterocyclyl, C$_{5-10}$ aryl or heteroaryl;

r is 0, 1 or 2;

R$_7$ is hydrogen, C$_{1-6}$ alkyl, C$_{1-6}$ alkoxy, C$_{3-7}$ cycloalkyl or C$_{1-3}$ alkyl-C$_{3-7}$ cycloalkyl;

R$_8$ is hydrogen, C$_{1-6}$ alkyl, C$_{1-6}$ alkyloxo, C$_{1-6}$ alkoxy, amino, C$_{1-6}$ alkylamino, C$_{1-6}$ aminoalkyl, C$_{3-7}$ cycloalkyl, C$_{1-3}$ alkyl —C$_{3-7}$ cycloalkyl or heterocyclyl;

each of R$_9$ and R$_{10}$ is independently hydrogen, C$_{1-6}$ alkyl, C$_{1-6}$ alkoxy, C$_{3-6}$ cycloalkyl, C$_{1-3}$ alkyl—C$_{3-6}$ cycloalkyl, or —(SO$_2$)—C$_{1-3}$ alkyl;

each of the heteroaryls is a 5- to 10-membered single or fused ring containing one or more heteroatoms selected from the group consisting of N, O, S and a combination thereof, and each of the heterocyclyls is a 3- to 10-membered single or fused ring containing one or more heteroatoms selected from the group consisting of N, O, S and a combination thereof;

one or more than one hydrogen of each of the cycloalkyls and heterocyclyls may be unsubstituted or substituted with hydroxyl, oxo, halo, cyano, nitro, C$_{1-6}$ alkyl, C$_{1-6}$ hydroxyalkyl, C$_{1-6}$ haloalkyl, C$_{1-6}$ alkoxy, formyl, C$_{1-6}$ alkylformyl, carboxy, C$_{1-6}$ alkylcarboxy, amino, C$_{1-6}$ alkylamino, di(C$_{1-6}$ alkyl)amino, carbamoyl, C$_{1-6}$ alkylcarbamoyl or di(C$_{1-6}$ alkyl)carbamoyl; and one or more than one hydrogen of each of the aryls and heteroaryls may be unsubstituted or substituted with hydroxyl, oxo, halo, cyano, nitro, C$_{1-6}$ alkyl, C$_{1-6}$ alkoxy, C$_{1-6}$ hydroxyalkyl, C$_{1-6}$ haloalkyl, pyrazinyl, formyl, C1-6 alkylformyl, carboxy, C1-6 alkylcarboxy, amino, C$_{1-6}$ alkylamino, di(C$_{1-6}$ alkyl)amino, carbamoyl, C$_{1-6}$ alkylcarbamoyl, di(C$_{1-6}$ alkyl)carbamoyl or C$_{1-6}$ alkylsulfonyl.

2. The compound of Chemical Formula 1 according to claim 1, wherein R$_1$ is hydrogen or hydroxyl {herein, if Y is N, R$_1$ is null};

X is CHR$_4$;

Y is N or C;

l is 0, 1 or 2;

R$_1$ is hydrogen or hydroxyl, cyano or C$_{1-6}$ alkyl {herein, if Y is N, R$_1$ is null};

R$_2$ is

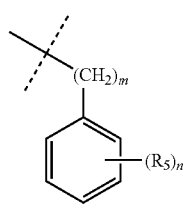

or heteroaryl;

R$_4$ is hydrogen;

m is 0, 1 or 2;

n is 0, 1, 2, or 3;

each of R$_5$ is independently —Z—(CH$_2$)$_p$—R$_6$, halo, or C$_{1-6}$ hydroxyalkyl;

Z is —O—or null;

p is 0, 1, 2, or 3;

R$_6$ is hydrogen, hydroxyl, —OR$_8$, —NR$_9$R$_{10}$, azido, C$_{1-6}$ dihydroxyalkyl, heterocyclyl, or heteroaryl;

R$_8$ is hydrogen, C$_{1-6}$ alkyl, or heterocyclyl;

each of R$_9$ and R$_{10}$ is independently hydrogen, C$_{1-6}$ alkyl or C$_{3-6}$ cycloalkyl;

a tautomer thereof, a stereoisomer thereof and their mixture, or a pharmaceutically acceptable salt thereof.

3. The compound according to claim 1, wherein the compound of Chemical Formula 1 is selected from a group consisting of:

(1) 2-(4-(2,6-difluoro-4-(2-methoxyethoxy)phenyl)piperazin-1-yl)-7,8-dihydro-3Hpyrano[4,3-d]pyrimidin-4(5H)-one, (2) 2-(4-(2,6-difluoro-4-(2-morpholinoethoxy)phenyl)piperazin-1-yl)-7,8-dihydro-3Hpyrano[4,3-d]pyrimidin-4(5H)-one, (3) 2-(4-(2,6-difluoro-4-(2-(piperidin-1-yl)ethoxy)phenyl)piperazin-1-yl)-7,8-dihydro-3H-pyrano[4,3-d]pyrimidin-4(5H)-one, (4) 2-(4-(2,6-difluoro-4-(2-hydroxyethoxy)phenyl)piperazin-1-yl)-7,8-dihydro-3Hpyrano[4,3-d]pyrimidin-4(5H)-one, (5) 2-(4-(4-(2,3-dihydroxypropoxy)-2,6-difluorophenyl)piperazin-1-yl)-7,8-dihydro-3H-pyrano[4,3-d]pyrimidin-4(5H)-one, (6) 2-(4-(2,6-difluoro-4-((4-methylpiperazin-1-yl)methyl)phenyl)piperazin-1-yl)-7,8-dihydro-3H-pyrano[4,3-d]pyrimidin-4(5H)-one, (7) 2-(4-(2,6-difluoro-4-(1-hydroxyethyl)phenyl)piperazin-1-yl)-7,8-dihydro-3Hpyrano[4,3 -d]pyrimidin-4(5H)-one, (8) 2-(4-(2,6-difluoro-4-(2-methoxyethoxy)phenyl)-4-hydroxypiperidin-1-yl)-7,8-dihydro-3H-pyrano[4,3-d]pyrimidin-4(5H)-one, (9) 2-(4-(2-methyl-2H-tetrazol-5-yl)piperidin-1-yl)-7,8-dihydro-3H-pyrano[4,3 -d]pyrimidin-4(5H)-one,

(10) 2-(4-(2,6-difluoro-4-(2-oxo-2-(piperidin-1-yl)ethoxy)phenyl)piperazin-1-yl)-7,8-dihydro-3H-pyrano[4,3-d]pyrimidin-4(5H)-one;

(11) 2-(4-(2,6-difluoro-4-(2-methoxyethoxy)phenyl)piperidin-1-yl)-7,8-dihydro-3Hpyrano[4,3 -d]pyrimidin-4(5H)-one,

(12) 2-(4-(4-(2-(diethylamino)ethoxy)-2,6-difluorophenyl)piperazin-1-yl)-7,8-dihydro-3H-pyrano[4,3-d]pyrimidin-4(5H)-one,

(13) 2-(4-(4-(2-(1H-imidazol-1-yl)ethoxy)-2,6-difluorophenyl)piperazin-1-yl)-7,8-dihydro-3H-pyrano[4,3-d]pyrimidin-4(5H)-one, a tautomer thereof, a stereoisomer thereof and their mixture, or a pharmaceutically acceptable salt thereof.

4. A pharmaceutical composition comprising the compound of Chemical Formula 1 according to claim 1, a tautomer thereof, a stereoisomer thereof and their mixture, or a pharmaceutically acceptable salt thereof as an active ingredient.

5. The pharmaceutical composition according to claim 4, which further comprises a pharmaceutically acceptable carrier, diluent, or excipient.

* * * * *